United States Patent [19]

Levy

[11] Patent Number: 5,050,735
[45] Date of Patent: Sep. 24, 1991

[54] SPECIMEN STRIP PACKAGE

[76] Inventor: Abner Levy, 325 N. Oakhurst Dr., Beverly Hills, Calif. 90210

[21] Appl. No.: 552,332

[22] Filed: Jul. 13, 1990

Related U.S. Application Data

[63] Continuation of Ser. No. 446,613, Dec. 6, 1989, abandoned, which is a continuation of Ser. No. 244,490, Sep. 14, 1988, abandoned, which is a continuation-in-part of Ser. No. 112,283, Oct. 26, 1987, abandoned.

[51] Int. Cl.⁵ .............................................. B65D 85/48
[52] U.S. Cl. .................................. 206/456; 128/630; 206/363; 206/472; 206/489; 206/569; 435/810; 436/808
[58] Field of Search ................... 206/63.3, 223, 231, 206/361, 362.4, 363, 370, 438, 449–456, 472, 482, 490–492, 489, 569, 570; 128/630, 757, 759; 435/810; 436/808; 229/40, 73, 87 R, 92.1, 92.3, 92.7, 92.8; 40/158 R, 159

[56] References Cited

U.S. PATENT DOCUMENTS

| | | | |
|---|---|---|---|
| 730,933 | 6/1903 | Lawson | 229/92.7 |
| 907,477 | 12/1908 | Drees | 229/92.3 |
| 1,141,172 | 6/1915 | Clark | 229/92.8 |
| 2,298,601 | 10/1942 | Tremblett | 229/92.8 |
| 2,559,776 | 7/1951 | Larzelere | 229/92.1 |
| 2,625,315 | 1/1953 | Fehrenkamp | 229/DIG. 4 |
| 2,985,288 | 5/1961 | Reich | 206/363 |
| 3,281,050 | 10/1966 | Suchodolski | 229/DIG. 4 |
| 4,078,656 | 3/1978 | Crane et al. | 206/456 X |
| 4,244,511 | 1/1981 | Coleman | 229/92.1 |

FOREIGN PATENT DOCUMENTS

| | | | |
|---|---|---|---|
| 18858 | 5/1904 | Sweden | 229/92.3 |
| 102650 | 12/1916 | United Kingdom | 229/92.8 |
| 437411 | 10/1935 | United Kingdom | 229/92.8 |

Primary Examiner—Bryon P. Gehman
Attorney, Agent, or Firm—Beehler & Pavitt

[57] ABSTRACT

A specimen kit for collection, preservation and dispatch of smear specimens collected on a glass slide makes use of a single sheet of package material having short fold-over panels at opposite end edges and long fold-over overlapping panels at the side edges, in this way to form a relatively long flat package. Transversely extending lines of perforations make possible separating the long flat package into one relatively shorter reusable package with opposite end panels and a throw away sheet. One of the end panels of the shorter reusable package has a specially formed retainer for securing a transparent specimen slide in place. The panel is additionally provided with a window through which is revealed information pertaining to the specimen on the slide.

15 Claims, 3 Drawing Sheets

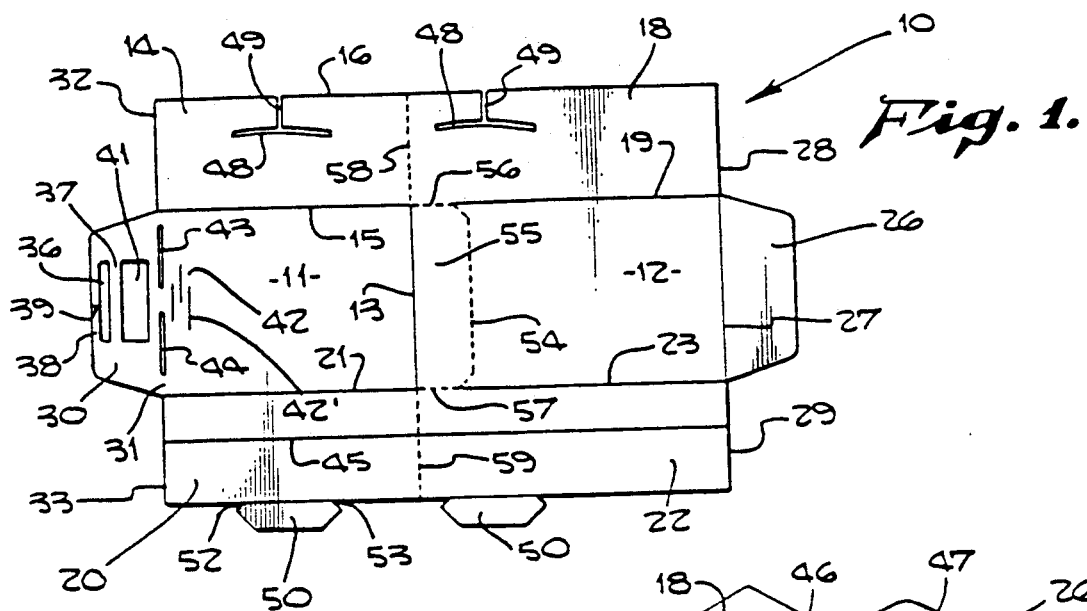
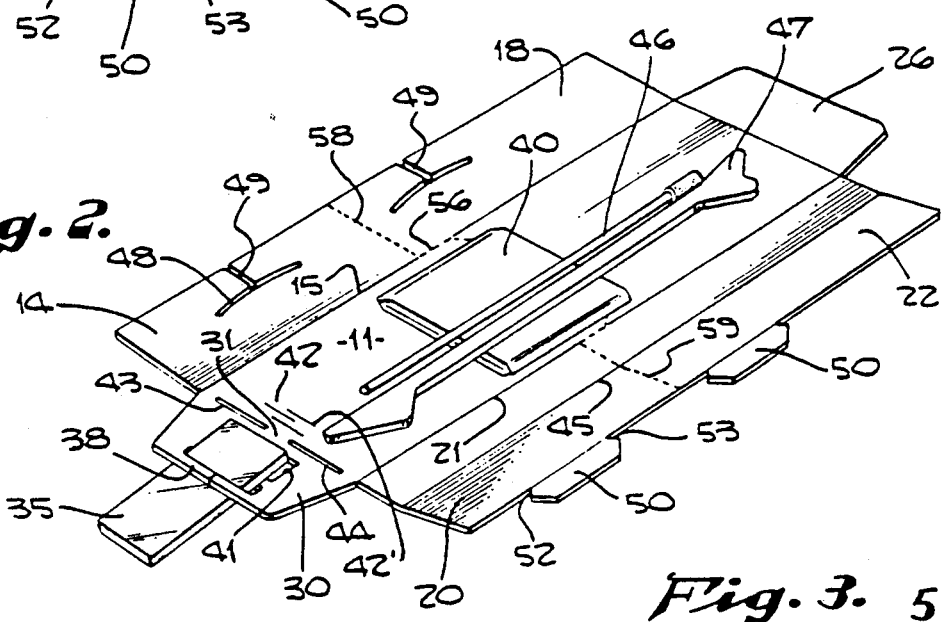
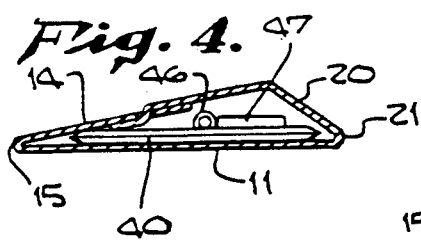
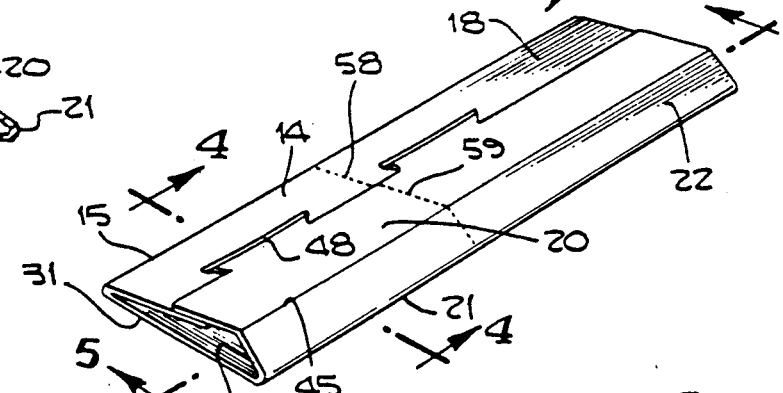
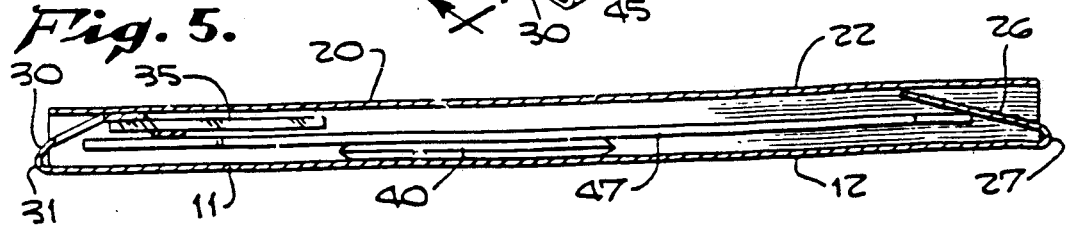

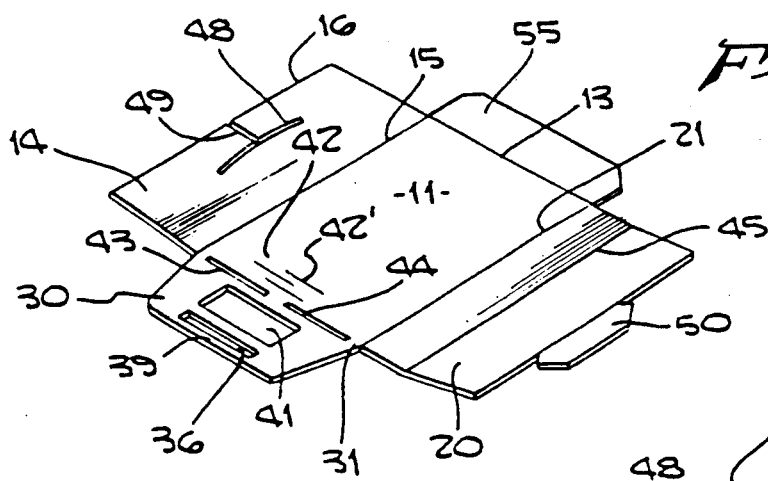
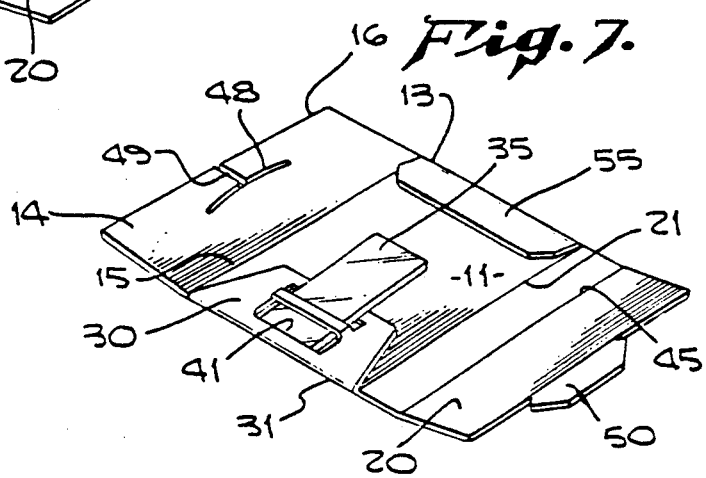
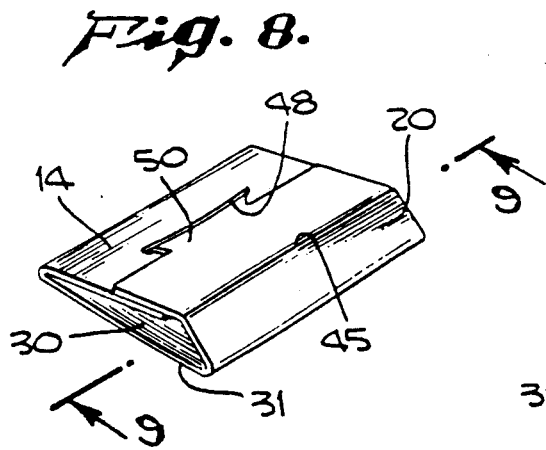
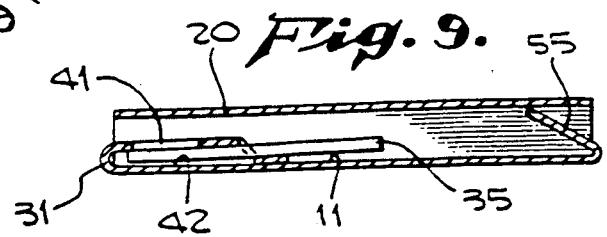
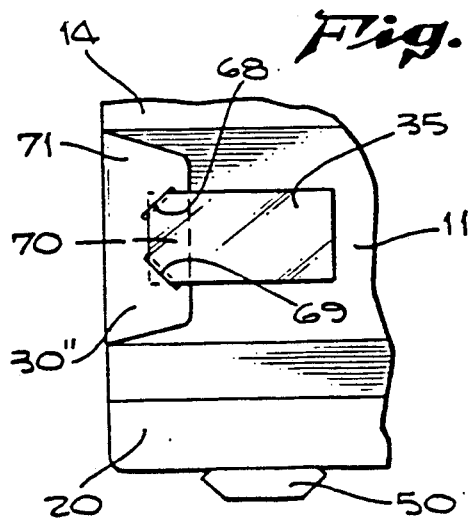
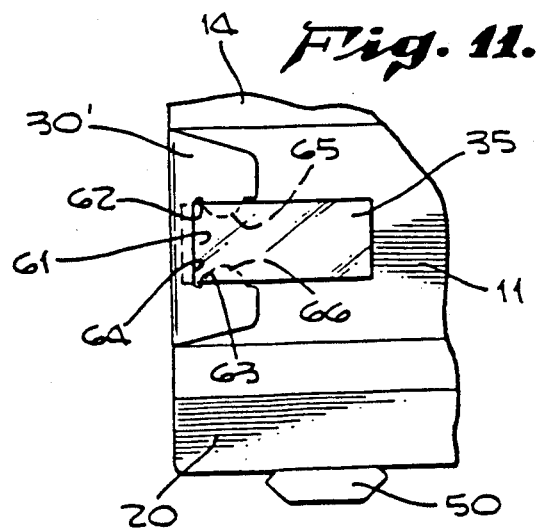

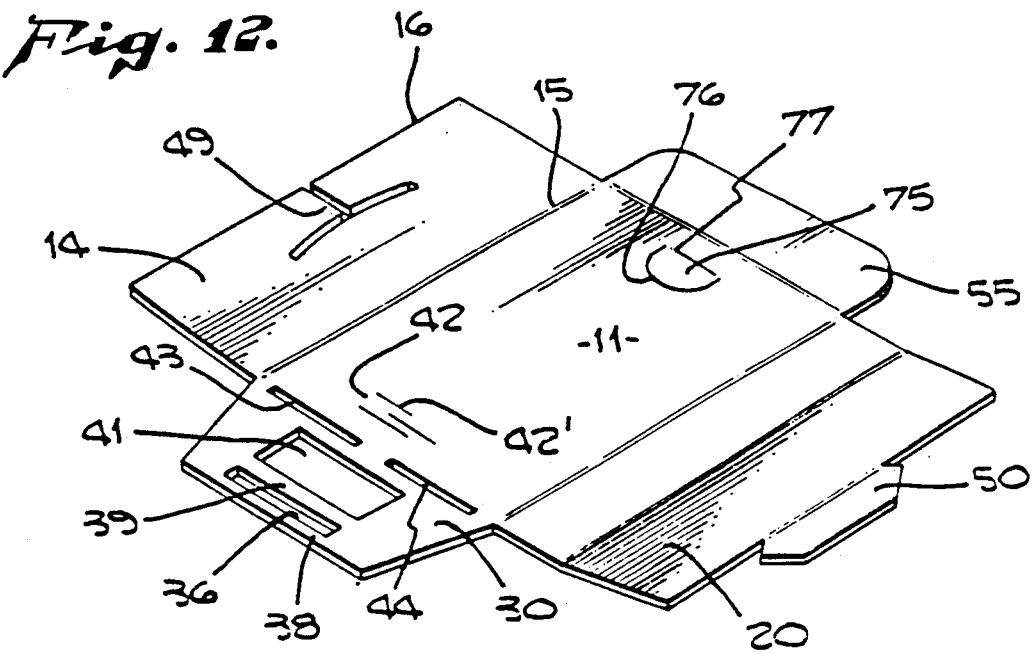
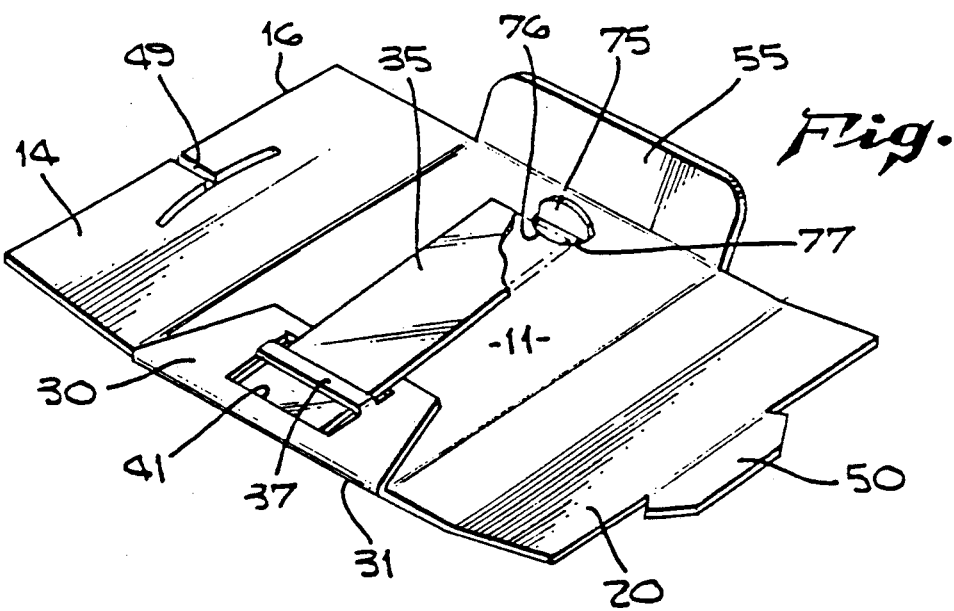
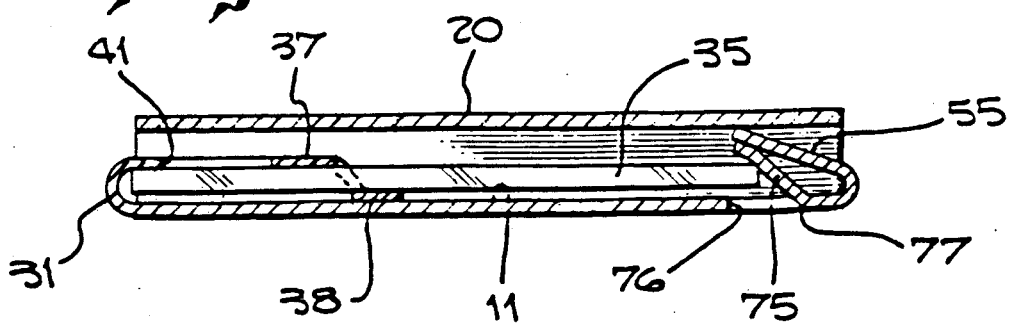

SPECIMEN STRIP PACKAGE

This application is a continuation of Ser. No. 446,613, filed Dec. 6, 1989, now abandoned, which is a continuation of Ser. No. 244,490, filed Sep. 14, 1988, now abandoned, which is a continuation-in-part of Ser. No. 112,283, filed Oct. 26, 1987, now abandoned.

For the handling of specimens for laboratory analysis in the medical and related fields, current practice is to have as much of the necessary paraphernalia as possible of a disposable character. Although biological and medical specimens in the final stage ready for microscopic or other examination may be compact and require little space for preservation and handling, that circumstance may not prevail during preparation for and collection of the specimen This is to say that for the collection of a specimen, the technician frequently has need for instruments, swabs, disinfectants, patches and the like, necessary for requiring the needed scraping, tissue or fluid accumulation which, once having been used, is no longer needed and can be disposed of.

Conversely, the specimen itself whether one for microscopic examination or chemical analysis, need only be very small, needs only modest means for preservation and requires a correspondingly small package in which to preserve it and deliver it for analysis.

It is therefore among the objects of the invention to provide a new and improved reusable-type package for acquisition and retention of a specimen, parts of which are readily disposable when no longer needed.

Another object of the invention is to provide a new and improved reusable package for the acquisition and retention of a specimen, which features a relatively larger package in which all necessary paraphernalia needed for acquisition of the specimen can be carried, but which is separable so as to leave only a relatively smaller package for the finally acquired specimen, by means of which it can be delivered to a laboratory for analysis.

Another object of the invention is to provide a new and improved reusable-type specimen package wherein an effective mounting for a specimen slide is provided in such manner that it is handily located and well protected during both the collecting stage as well as the final use stage and which is accompanied by adequate and readily available means for identification.

Still another object of the invention is to provide a new and improved reusable-type specimen package which is compact when filled with the necessary paraphernalia, and further which is of such character that it can be divided into a smaller compact package for containing only the specimen, permitting the surplus packaging to be disposed of.

Still further among the objects of the invention is to provide a new and improved reusable-type specimen package of adequate proportions to contain collection of paraphernalia and the final specimen, which is easily and readily manipulatable during collection and final disposition, relatively inexpensive and readily disposable as to those portions which may no longer be needed once the specimen has been collected and ready for delivery to the laboratory.

With these and other objects in view, the invention consists of the construction, arrangement and combination of the various parts of the device serving as examples only of one or more embodiments of the invention, whereby the objects contemplated are attained, as hereinafter disclosed in the specification and drawings, and pointed out in the appended claims.

IN THE DRAWINGS

FIG. 1 is a plan view of the sheet of material cut to shape and size for the package.

FIG. 2 is a perspective view of the sheet of material equipped for initial packaging.

FIG. 3 is a perspective view of the initially formed package.

FIG. 4 is a cross-sectional view on the line 4—4 FIG. 3.

FIG. 5 is a longitudinal sectional view on the line 5—5 of FIG. 3.

FIG. 6 is a perspective view of that portion of the sheet of material used for the final package.

FIG. 7 is a view similar to FIG. 6, but partly folded over for packaging.

FIG. 8 is a perspective view of a completed final package.

FIG. 9 is a longitudinal sectional view on the line 9—9 of FIG. 8.

FIG. 10 is a fragmentary plan view of a second form of the sheet of material as equipped for packaging.

FIG. 11 is a fragmentary plan view of a third form of the sheet of material as equipped for packaging.

FIG. 12 is a perspective view of that portion of the sheet of material used for the final package of a modified form of the device.

FIG. 13 is a perspective view similar to FIG. 12 wherein the slide is shown in place.

FIG. 14 is a cross-sectional view of the final package of the modified form of FIGS. 12 and 13.

In an embodiment of the invention chosen for the purpose of illustration there is shown a sheet of packaging material for assembly into a specimen package indicated generally by the reference character 10, which consists essentially of a single sheet of package material specially cut for folding in a distinctive fashion. The package is made up of two central base portions 11 and 12 separated by a transverse fold line 13. The two base portions together form, in effect, a long rectangular bottom for the package in its initial form. On one side of the base portion 11 is a side panel 14 with a captive side edge joined by a fold line 15 to a corresponding side edge of the base panel 11, leaving a free edge 16.

Similarly, for the base portion 12 there is a side panel 18 with a captive side edge joined by a fold line 19 to a corresponding side edge of the base portion 12. The fold lines 15 and 19 are continuous with respect to each other forming one fold line for the combined side panels 14 and 18 permitting them to be folded over the initially joined base portions 11 and 12.

On the opposite side of the base portion 11 is a side panel 20 having a captive edge joined to a corresponding edge of the base portion 11 along a fold line 21. Again, for the base portion 12 there is a side panel 22 joined along a fold line 23 to a corresponding edge of the base portion 12. It is of consequence to note in this connection that the combined width of the side panels 14 and 20 is materially greater than the width of the corresponding base portion 11. Similarly, the combined width of the side panels 18 and 22 is materially greater than the width of the base panel 12.

At the free end of the base portion 12 is an end panel 26 joined at its captive edge to a corresponding edge of the base along a fold line 27. The fold line 27 is in alignment with an end edge 28 of the side panel 18 and a similar end edge 29 of the side panel 22.

At the opposite end of the package there is another end panel 30 joined at its captive edge to a corresponding edge of the base portion 11 along a fold line 31. The fold line 31 is in alignment with an end edge 32 of the side panel 14 and a corresponding end edge 33 of the side panel 20.

One of the end panels, namely, the end panel 30 as shown, provides for attachment of a specimen strip 35, a specimen strip customarily being a transparent glass or plastic strip for reception of the physical specimen for which analysis is sought. As shown in the form of invention of FIG. 1, the end panel 30 is provided with a slot 36 long enough to accommodate the width of the specimen strip and wide enough to comfortably accommodate the thickness.

In the embodiment shown there is a bar 37 forming one side of the slot 36 and a second bar 38 forming the other side, the bar 38 being separated by a slit 39. At the relative midportion of the end panel 30 there is provided a window 41. The window has a length approximately equal to the length of the slot 36 and a width substantially greater. Beneath the window is a space 42 which is provided for identification of the specimen which is to be collected on the specimen strip 35.

By providing retention means on the end panel 30 for the specimen strip 35 in the form and manner described, the specimen strip can be attached to the end panel when the panel is in open position, and then the tab with the strip swung over the corresponding face of the bottom portion 11. Insertion and removal of the strip can also take place when the end panel is folded over. By having the specimen strip capable of being lifted with the end panel, there is ready access to the space 42 for specimen identification insignia, marks or marking 42', after which it is covered over by replacement of the strip and end panel.

It is additionally noteworthy to have cuts 43 and 44 extending partway along the length of the fold line 31. With the fold line cut in this fashion, the end panel and connected specimen strip can be more readily compacted in final position during the packaging. There is a comparable advantage in the provision of a score line 45 operable when the initial package is closed. The end panel 30 with a single window 41 is by way of example only. On occasion two windows each with a strip may be preferred. The side panels 14 and 20 also provide package material where windows and strip may be located, if desired, assisted if need be with cuts like the cuts 43 and 44 which assist the end panel 30.

For closing and holding the package in closed position, the side panel 14 is provided with a slightly arcuate slit 48, with an escape slit 49 extending to the free edge 16. There is a comparable slit and escape slit for the side panel 18. On the opposite side of the base portion 11, the side panel 20 is provided with a flap 50 on a corresponding free edge 51. The side panel 20 has notches 52 and 53 at opposite ends of the flap 50. The notches determine an effective length for the flap as being slightly greater than the length of the slit 48 when the flap is interlocked with the slit. The side panel 22 is similarly equipped.

It has been found advantageous to have the aggregate width of the side panel 20 and the distance between the fold line 15 and the slit 48 slightly greater than the width of the base portion 11. Dimensioned as described, coupled with a slight folding at the score line 45, provides for a space beneath the side panels 14 and 20 when they are folded over each other to allow for accommodation not only of the specimen strip 35, but other paraphernalia which may be initially contained within the package such, for example, as a swab 46, tongue depressor 47 and fixative package 40.

There is additionally provided a line of perforations between the base portion 11 together with its side panels 14 and 20, and the base portion 12 together with its side panels 18 and 22. A central section 54 of the line of perforations separates the base portion 12 from an auxiliary end panel 55. Side sections 56 and 57 of the line of perforations defines side edges of the auxiliary end panel 55. A section 58 of the line of perforations separates the side panels 14 and 18 and a section 59 separates side panels 20 and 22.

When the full size of the package as shown in FIG. 3 is no longer needed, the package is separated along the lines of perforations just described so that the base portion 11 with its newly acquired auxiliary end panel 55 can be made into a smaller separate package as shown in FIG. 8 completed by the presence of the folded-over side panels 14 and 20. The base portion 12, with its side panels 18 and 22 and end panel 26 being no longer needed, may be disposed of, together with such paraphernalia as may initially have been needed. Under these circumstances, the smaller of the packages which contains the specimen strip 35 and its identification is readily closeable for transportation and storage until needed.

In a second form of the invention, an end panel 30' is shown provided with a window 61 formed by side edges 62 and 63 with an end edge 64. Tabs 65 and 66 are located on corresponding side edges 62 and 63 and provide for retention of the specimen strip 35. There is abundant space beneath the window for use in identification.

In another form of the device, an end panel 30'' is shown provided with diagonally disposed slits 68, 69 for retention of the specimen strip 35. A space 70 on the corresponding face 71 of the end panel serves for use in identification of the specimen.

In the form of the device of FIGS. 12, 13 and 14, use is made of a holding tab 75 for additional retention of the otherwise free end of the specimen strip 35. The holding tab shown by way of example is cut from the base portion 11 along an arcuate line 76. A folding line 77 of the holding tab is at a location adjacent to or slightly beyond the position the free end of the specimen strip will have when the package is closed for shipping. In this position the holding tab will be capable of pressing firmly against the specimen strip, with the assistance of the auxiliary end panel 55 and one or another of the side panels 14, 20. Retention of the free end edge of the specimen strip is effective in preventing endwise shifting when packaged.

While particular embodiments of the present invention have been shown and described, it will be obvious to those skilled in the art that changes and modifications may be made without departing from the invention in its broader aspects and, therefore, the aim of its attendant claims is to cover all such changes and modifications as fall within the true spirit and scope of this invention.

Having described the invention, what is claimed as new in support of Letters Patent is as follows:

1. A specimen package assembly for containment of a specimen strip and specimen identification marks, said package assembly comprising a sheet of package material in initial form having a central base portion of relatively long rectangular configuration with long side edges and short end edges, a first side panel having a captive edge joined to an adjacent side edge of the base portion at a fold line and a free edge, a second side panel having a captive edge joined to the other side edge of the base portion at a fold line and a free edge, a first end panel having a captive edge joined at an adjacent end edge of the base portion and a free edge, a second end panel having a captive edge joined to the other end edge of the base portion and a free edge, one of said end panels having retaining means engaging one end of said specimen strip with a substantial portion of said strip extending beyond said free edge of said one of said end panels towards the other of said end panels, thereby to support and retain the specimen strip in a position overlying the central base portion, there being latching means adjacent free edges of said side panels for holding all said panels and aid specimen strip in packaged position, and an area of said central base portion receptive of specimen identification marks beneath a window in said one of said end panels.

2. A specimen package assembly as in claim 1 wherein there is a perforated line extending through said side panels and continuing through the base portion at a location spaced from the line through the side panels whereby to provide a secondary end panel for that portion of the package assembly containing said retaining means for the specimen strip, said perforated line being at a location where parts of the package are separated.

3. A specimen package assembly as in claim 1 wherein there is means forming a slot in a portion of the sheet of package material where the edge of the base portion joins the edge of that end panel which carries said retaining means for the specimen strip.

4. A specimen package assembly as in claim 1 wherein there is a lock slot adjacent the free edge of one of said side panels and a lock tab adjacent the free edge of the other of said side panels adapted to engage the lock slot and form a continuous cover for the corresponding area of the base portion, the effective width of said continuous cover being greater than the width of the base portion whereby to provide a space within said specimen package assembly.

5. A specimen package assembly as in claim 4 wherein there is a score line on one of said side panels parallel to and intermediate opposite side edges of said one of said side panels to enable bending of said one of said side panels when adjacent free edges of the side panels are in engagement.

6. A specimen package assembly for containment of a specimen strip and specimen identification marking, said package assembly comprising a sheet of package material in initial form having a central base portion of relatively long rectangular configuration with long side edges and short end edges, a first side panel having a captive edge joined to an adjacent side edge of the base portion at a fold line and a free edge, a second side panel having a captive edge joined to the other side edge of the base portion at a fold line and a free edge, a first end panel having a captive edge joined at an adjacent end edge of the base portion and a free edge, a second end panel having a captive edge joined to the other end edge of the base portion and a free edge, one of said end panels having retaining means for retention of the specimen strip in a position overlying the corresponding central base portion, said sheet adjacent said one of said panels having an area receptive of said specimen identification marking, there being means adjacent free edges of said side panels for holding all said panels and said specimen strip in packaged position, said retaining means having a window in the panel in which said means is located and a slot adjacent the window for insertion of the specimen strip to a location coincident with said window.

7. A specimen package assembly for containment of a specimen strip and specimen identification marking, said package assembly comprising a sheet of package material in initial form having a central base portion of relatively long rectangular configuration with long side edges and short end edges, a first side panel having a captive edge joined to an adjacent side edge of the base portion at a fold line and a free edge, a second side panel having a captive edge joined to the other side edge of the base portion at a fold line and a free edge, a first end panel having a captive edge joined at an adjacent end edge of the base portion and a free edge, a second end panel having a captive edge joined to the other end edge of the base portion and a free edge, one of said end panels having retaining means for retention of the specimen strip in a position overlying the corresponding central base portion, said sheet adjacent said one of said end panels having an area receptive of said specimen identification marking, there being latching means adjacent free edges of said side panels for holding all said panels and said specimen strip in packaged position, said retaining means having a window extending through said one end panel and tabs at outside edges of the window for engagement by said specimen strip.

8. A specimen package assembly as in claim 7 wherein there is a plurality of angularly disposed slits in said one of said end panels for reception and retention of the specimen strip, there being an area of said central base portion for identification marking.

9. A specimen package assembly as in claim 7 wherein there is a tab on said base portion at a location adjacent the free end of the specimen strip when said specimen strip is in position overlying the central base portion, said tab being adapted to assume a retention position overlying said specimen strip.

10. A specimen package assembly as in claim 9 wherein said retaining means comprises a cut-out portion of a panel adjacent one edge of the base portion and said tab is at a location adjacent a second end panel opposite said one end panel having the retaining means and is adapted to lie beneath said second end panel in closed position of said package assembly.

11. A specimen package assembly as in claim 7 wherein there is a tab comprising a cut-out section of said central base portion at a location adjacent the free end of the specimen strip when said specimen strip is in a position overlying the central base portion.

12. A specimen package assembly as in claim 11 wherein said tab is at a location adjacent a second end panel opposite said one end panel having the retaining means.

13. A specimen package assembly for containment of a specimen strip and specimen identification marks, said one package assembly comprising a sheet of package material in initial form having a central base portion, a plurality of side panels and end panels joined to said central base portion, one of said end panels having a free edge and retaining means engaging one end of said specimen strip with a substantial portion of said strip extending beyond said free edge thereby to support and retain the specimen strip in a position overlying the central base portion, there being latching means on said side panels for holding all said panels and said specimen strip in packaged position, such that said strip can be moved with said panel from a packaged position against said base portion to a raised position away from said base portion for easy grasping of said strip.

14. The specimen package of claim 13, further comprising an area of said central base portion receptive of specimen identification marks beneath a window in said one of said end panels such that said area is viewable through said strip in said packaged position when said strip is transparent.

15. The specimen package of claim 13 further comprising an area of said central base portion receptive of specimen identification marks beneath said one of said end panels.

* * * * *